(12) United States Patent
Li et al.

(10) Patent No.: US 7,209,228 B2
(45) Date of Patent: Apr. 24, 2007

(54) SCANNING APPARATUS

(76) Inventors: Perry Y. Li, 1076 Lovell Ave., Roseville, MN (US) 55113; Chuanqi Chen, 5101 Boarshead Rd., #338, Minnetonka, MN (US) 55345; Arthur G. Erdman, 1957 3rd St. SW., New Brighton, MN (US) 55112; Zhang Hong, 708 University Ave. SE., #22, Minneapolis, MN (US) 55414; John Byron Raymond, 10296 173rd St. W., Lakeville, MN (US) 55044

(*) Notice: Subject to any disclaimer, the term of this patent is extended or adjusted under 35 U.S.C. 154(b) by 35 days.

(21) Appl. No.: 10/712,802

(22) Filed: Nov. 12, 2003

(65) Prior Publication Data

US 2004/0246494 A1 Dec. 9, 2004

Related U.S. Application Data

(63) Continuation of application No. 09/426,385, filed on Oct. 25, 1999, now abandoned.

(51) Int. Cl.
G01N 21/01 (2006.01)
A61F 1/12 (2006.01)
A61B 19/00 (2006.01)

(52) U.S. Cl. ............... 356/244; 606/130; 606/107
(58) Field of Classification Search ........ 356/244–246, 356/373, 375, 376; 250/559.22, 559.23
See application file for complete search history.

(56) References Cited

U.S. PATENT DOCUMENTS

| | | | |
|---|---|---|---|
| 4,997,369 A * | 3/1991 | Shafir | 433/72 |
| 5,017,139 A * | 5/1991 | Mushabac | 433/109 |
| 5,030,839 A * | 7/1991 | van de Stadt | 250/559.15 |
| 5,050,608 A * | 9/1991 | Watanabe et al. | 600/429 |
| 5,078,140 A * | 1/1992 | Kwoh | 600/417 |
| 5,106,192 A * | 4/1992 | Tucker et al. | 356/477 |
| 5,131,844 A * | 7/1992 | Marinaccio et al. | 433/72 |
| 5,548,405 A * | 8/1996 | Motosugi | 356/601 |
| 5,697,939 A * | 12/1997 | Kubota et al. | 606/130 |
| 5,760,906 A * | 6/1998 | Sato | 356/602 |
| 5,762,458 A * | 6/1998 | Wang et al. | 414/1 |
| 5,810,765 A * | 9/1998 | Oda | 604/31 |
| 5,824,007 A | 10/1998 | Faraz et al. | |
| 5,847,528 A * | 12/1998 | Hui et al. | 318/568.1 |
| 5,891,034 A * | 4/1999 | Bucholz | 600/426 |
| 5,891,157 A * | 4/1999 | Day et al. | 606/130 |

(Continued)

OTHER PUBLICATIONS

J-P. Merlet, Parallel Manipulators: State of the art and Perspectives, May 1999, INRIA Sophia-Antipolis.*

(Continued)

*Primary Examiner*—Michael P. Stafira
(74) *Attorney, Agent, or Firm*—Merchant & Gould P.C.

(57) ABSTRACT

A scanning apparatus includes a support frame and a laser scanner mounted to the frame. A five bar closed loop spherical linkage supports a clamping device for retaining an object. The linkage moves the object through a scanning beam about a spherical surface to facilitate scanning of curved objects. The linkage is mounted on an arm rotatably mounted to the frame and the clamping device is rotatably mounted to the linkage to provide four degrees of freedom. Encoders and motors drive the linkage to provide accurate positioning and providing for digitizing the scanned object.

21 Claims, 12 Drawing Sheets

U.S. PATENT DOCUMENTS

| | | | | |
|---|---|---|---|---|
| 5,966,991 | A | * | 10/1999 | Gosselin et al. ............ 74/490.1 |
| 5,971,997 | A | * | 10/1999 | Guthrie et al. .............. 606/130 |
| 6,047,610 | A | * | 4/2000 | Stocco et al. ............ 74/479.01 |
| 6,064,759 | A | * | 5/2000 | Buckley et al. ............. 382/154 |
| 6,086,283 | A | * | 7/2000 | Ziegert ........................ 403/57 |
| 6,355,048 | B1 | * | 3/2002 | Hong et al. ................. 606/130 |

OTHER PUBLICATIONS

Ralph C. Merkle, A New Family of Six Degree of Freedom Positional Devices, 1994, Xerox Corporation.*

IEEE, On the Development of the Agile Eye, 1996, 1070-9932.*

Doyang Hong, Design of Adjustable spherical four-bar linkages as continuous paasive motion devices anatomic joints rehabilitation, 1996, ASME.*

Kealy R. Ham, Spherical Four-Bar Linkage mechanism for continuous passive movement rehabilitation treatment of the ankle, 1996, ASME.*

Gosselin et al., "On the Development of the Agile Eye," *IEEE Robotics & Automation Magazine.* pp. 29-37 (Dec. 1996).

Ham et al., "Spherical Four-Bar Linkage Mechanism for Continuous Passive Movement Rehabilitation Treatment of the Ankle." *Proceedings of The 1996 ASME Design Engineering Technical Conferences and Computers in Engineering Conference.* pp. 1-6 (Aug. 18-22, 1996).

Hong et al., "Design of Adjustable Spharical Four-Bar Linkages as Continuous Passive Motion Devices for Anatomic Joints Rehabilitation," *Proceedings of The 1996 ASME Design Engineering Technical Conference and Computers in Engineering Conference,* pp. 1-10 (Aug. 18-22, 1996).

Merkle, R., New Positional Device, "A New Family of Six Degree of Freedom Positional Devices," http://www.zyvex.com/nanotech/6dof.html. pp.1-12 (Printed Sep. 14, 2001).

Merlet, "Parallel manipulators: state of the art and perspectives," http://www-sop.inria∫r/saga/personnel/merlet/Eras/eras_de_lort.html. pp. 1-9 (Printed May 18, 1999).

"Kinematics and dynamics of parallel mechanisms and manipulators", http://wwwrobot.gmc.ulaval.cal, pp. 1-10 (Printed May 18, 1999).

Dec. 1996 Robotics and Automation Index and Abstracts, http://www.nesu.edu/IEEE-RAS/RAMissues/RAMissues/RAMvol03no04.html, pp.1-3 (Printed May 18, 1999).

* cited by examiner

SCANNING APPARATUS

This application is a continuation of U.S. patent application Ser. No. 09/426,385 filed Oct. 25, 1999, now abandoned.

BACKGROUND OF THE INVENTION

The present invention is directed to a digital scanner, and in particular to a digital scanner used for dental modeling employing a linkage moving the dental mold relative to the scanner in a curved pattern.

PRIOR ART

In the dental industry, a wax type material is used to make an impression of the profile of the teeth for the fabrication of dental bridges and crowns. A cast crown or bridge is made from the impressions. It is generally necessary to store the mold for extended periods of time, as may be required by codes and regulations. The storage of such castings can be a great expense for the dentist. The impressions require much space and must be stored in a controlled environment to preserve the impressions. The impressions may include imperfections due to improper casting technique. In addition, the mold may decay over time, failing to provide a long-time accurate record as may be required for future dental work.

It is possible using computer aided modeling and scanning to overcome these problems. Such digitized images may then be stored and utilized to recreate the impression needed for making crowns, bridges or for other dental work. Digital storage of the patient's dental records overcomes the problems associated with storing the physical impressions. Such digitized images of the teeth may be utilized for the same diagnostics as other models and recreating a physical model. Accurate measurements may also be made from the digitized model for other applications, such as use by orthodontists for fitting braces and other appliances. The dental images are long lasting and do not decay over time. Moreover, many dental images may be stored on a CD-ROM or other suitable storage device, taking up only computer storage disk space rather than physical space required for storing the cast dental impressions.

Although scanner system have been developed which are capable of digitizing the image from scanning a dental mold, the time required for such scanning may take several hours. Many sweeps are needed in order to accumulate sufficient data to fully digitize the cast impression. Typical techniques for digital scanning are based on systems that have independent rectilinear movement, typically along the X, Y or Z directions. It will be appreciated that the nature of the arrangement of teeth makes controlling and coordinating the typical rectilinear scanning techniques difficult. The teeth provide many arcing surfaces, as well as being arranged in an arcing configuration. These crevices and uneven surfaces may be difficult to accurately scan with a typical arrangement moving the scanner linearly relative to the impression. Scanner systems employing rectilinear motion during scanning accumulate far more data than is necessary to create an accurate digital model, adding to the scanning time. It can be appreciated that if an arcing sweep could be made across the dental impression, scanning could be more efficient.

In order to achieve arcing movement, a linkage must be developed for moving the impression or scanner relative to one another in an arcing pattern within the focal range of the scanner. Typically, laser scanners have a very small depth of field so that the dental impression must be held within that range relative to the scanner in order to perform the scanning for digitizing. Many mechanisms have difficulty maintaining the object in the depth of field while moving the object through the required scans without interfering with the scanning beam. In addition, any linkage must be capable of moving the impression and scanner relative to one another so that the entire surface can be scanned. It is necessary that the impression be scanned without the linkage blocking the scanner at any particular position and losing data. The linkage mechanism must also provide the support necessary to prevent inaccuracies due to flexing and compounded tolerances leading to errors that may distort the accuracy of the digital model. As the scan is conducted, any inaccuracies could result in an unusable digital model.

It is preferable for each dentist to have a system scanning in the office so that impressions do not need to be sent out for scanning. The size and cost of the system is very important. Such a digitizing scanning system is preferably sufficiently compact that it may be stored and placed on the desktop in an office. However, the mechanism necessary to move the scanner and impression relative to one another to achieve the accurate and full scanning provides challenges for the linkage design. In addition, the mechanism may require multiple drivers for achieving the multiple degrees of freedom that may be necessary in order to move the scanner and impression relative to one another to achieve full and accurate scanning.

It can be seen then that an improved digitizing system is needed. Such a system should replace the need for physical dental impressions and the problems associated with storage of such impressions. Such a system should also provide for accurate scanning in a reduced time frame that provides for curved paths of motion over the dental impression. The system should also be compact so that it may be stored easily in a dental office and achieve a degree of speed and accuracy that improves over linear scanning techniques. The present invention addresses these as well as other problems associated with scanning and storage of dental impressions.

SUMMARY OF THE INVENTION

The present invention is directed to a scanning system and in particular to a scanning apparatus having a spherical five bar serial closed loop linkage adapted for supporting dental molds to be scanned. The scanning system includes a scanner device, such as a laser scanner, supported by a framework. A linkage is used to support an object to be scanned within the focal range of the laser scanning device. The linkage moves the object relative to the scanning beam so that the object's surface may be measured and digitized for improved storage. The linkage is preferably a five bar closed loop spherical serial linkage wherein the axis of rotation through each joint intersects at a center of a sphere defined by the linkage. The linkage has two degrees of freedom and two drive motors for positioning the linkage. In addition, the linkage is mounted on another arm for rotation relative to the scanning device in a preferred embodiment. The object to be scanned may also be rotatably or slidably mounted to and supported on the linkage so that its orientation may be changed in addition to the freedom provided by the linkage motion. The linkage provides for scanning in a curved manner over the surface of the object and is well suited for scanning objects such as dental molds, having arcing shapes which are better suited for curved scanning paths of motions.

The linkage includes a first ground link rotatably mounted relative to the supporting arm. The ground link is mounted at a first end to a first end of a second link at a first joint. The first joint has an axis of rotation intersecting the center of the rotational sphere defined by the spherical linkage. A second end of the second link connects to a first end of a third link through a second joint also having an axis of rotation intersecting with the axis of rotation for the first joint and the other joints at the center of the sphere. The second end of the third link connects to a first end of the fourth link at a third joint, also having an axis of rotation intersecting at the center of the spherical linkage. A second end of the fourth link connects at a fourth joint to a first end of a fifth link. The axis of rotation between the fourth and fifth links extends to the intersection at the center of the sphere. A second end of the fifth link pivotally mounts to the first ground link at a second location. The axis of rotation extending through this joint intersects with the four axes of rotation of the other four joints at the center of the sphere.

A clamping mechanism retains an article holder, such as a dental mold tray holding a dental mold, at the exterior of the sphere in a first embodiment to move the dental mold through the laser beam of the scanner. With this configuration, the links do not pass through the scanning beam so that an uninterrupted scan of the surface of the object may be accomplished utilizing the linkage.

In a preferred embodiment, the joints include bearing assemblies having one or more sets of bearings supporting rotational shafts providing the axes of rotation for the joints between the various links. In a preferred embodiment, the clamping mechanism for holding the dental mold tray is positioned between the third and fourth link with the dental mold substantially aligned with the axis extending through the joint between the third and fourth links. Motors drive the second and fifth links relative to the first link to position the linkage. However, it can be appreciated by those skilled in the art that the clamping mechanism and the drive motors may be mounted at other locations. As the spherical five bar closed loop serial linkage has two degrees of freedom, two motors are required to position the links at any desired position. In addition, the clamping mechanism for the dental mold tray includes a motor to rotate the dental mold tray. The dental mold can be rotated relative to the linkage for improved scanning. The entire linkage may also be rotated relative to the scanner by rotating the arm also serving as a first link relative to the frame. Bearings at each frame upright support the arm and at least one motor drives the arm through rotational positioning. The rotational axis of the arm extends substantially through the dental mold, so the scanned object remains within the depth of field of the scanner as the arm is rotated.

The present invention provides for improved scanning with curved paths of motion. As the linkage moving the object to be scanned is a spherical-type linkage, there are improved economies of space provided by the linkage as it is more compact than linear scanners performing the same scans. This configuration also decreases the likelihood that the linkage will interfere with the scanning beam. Placement of the supported article to be scanned exterior of the linkage sphere allows the linkage to have a smaller diameter. In addition, the scanning system provides four degrees of freedom for improved scanning angles and precision that are not possible with prior art systems. As the linkage is a closed loop serial linkage, greater support is provided between the links, which are all supported on both ends, so that flexure due to loads placed on the linkage is diminished as compared to open ended serial type linkages. The curved scanning pattern for curved object shapes provides for faster, more efficient scanning than linear methods, which must have far more scanning passes and data than are required with a nonlinear path of motion.

These features of novelty and various other advantages which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

Referring now to the drawings, wherein like reference letters and numerals indicate corresponding structure throughout the several views.

DETAILED DESCRIPTION OF THE PREFERRED EMBODIMENT(S)

Figure 1:
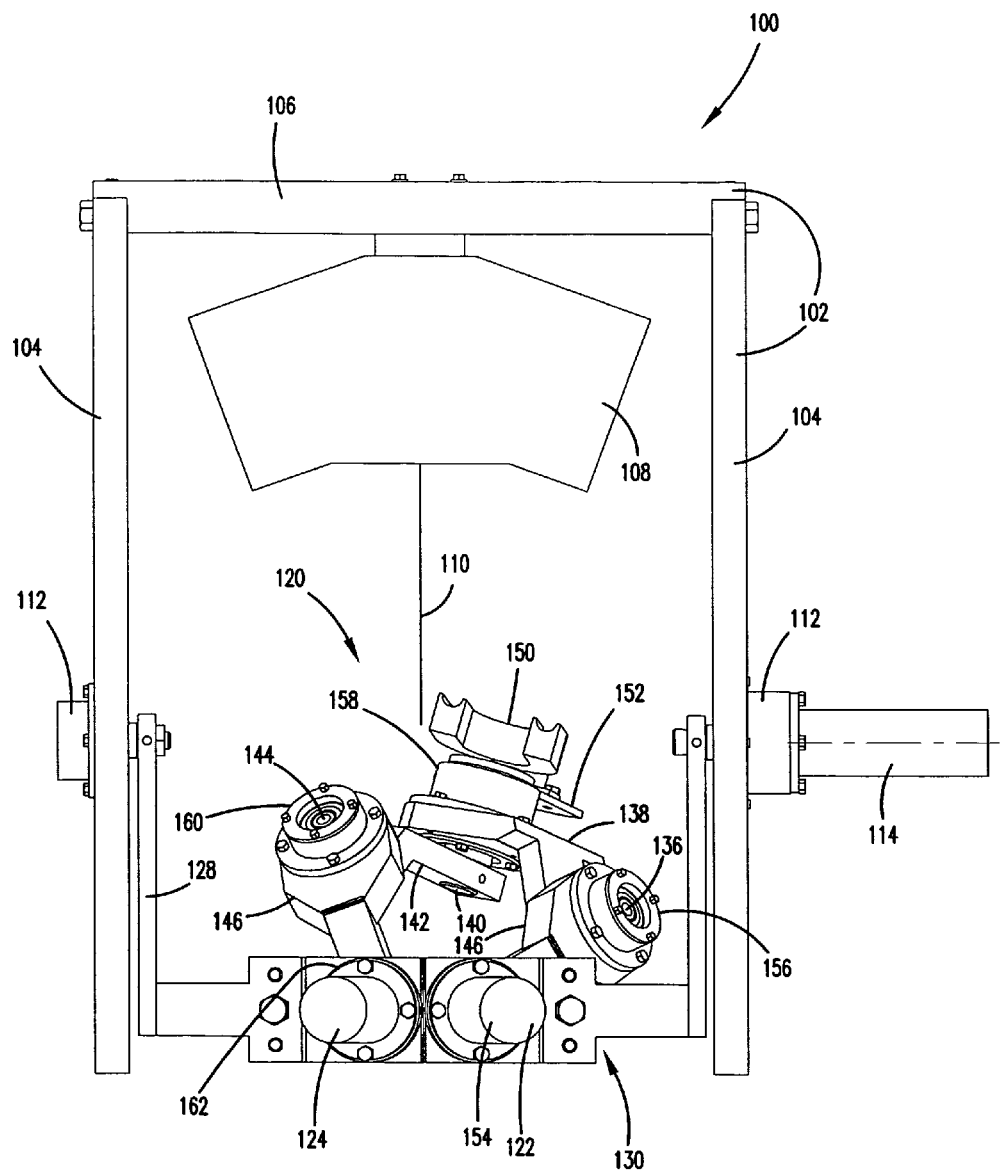
FIG. 1 shows a front elevational view of a digital scanner apparatus according to the principles of the present invention.
Figure 2:
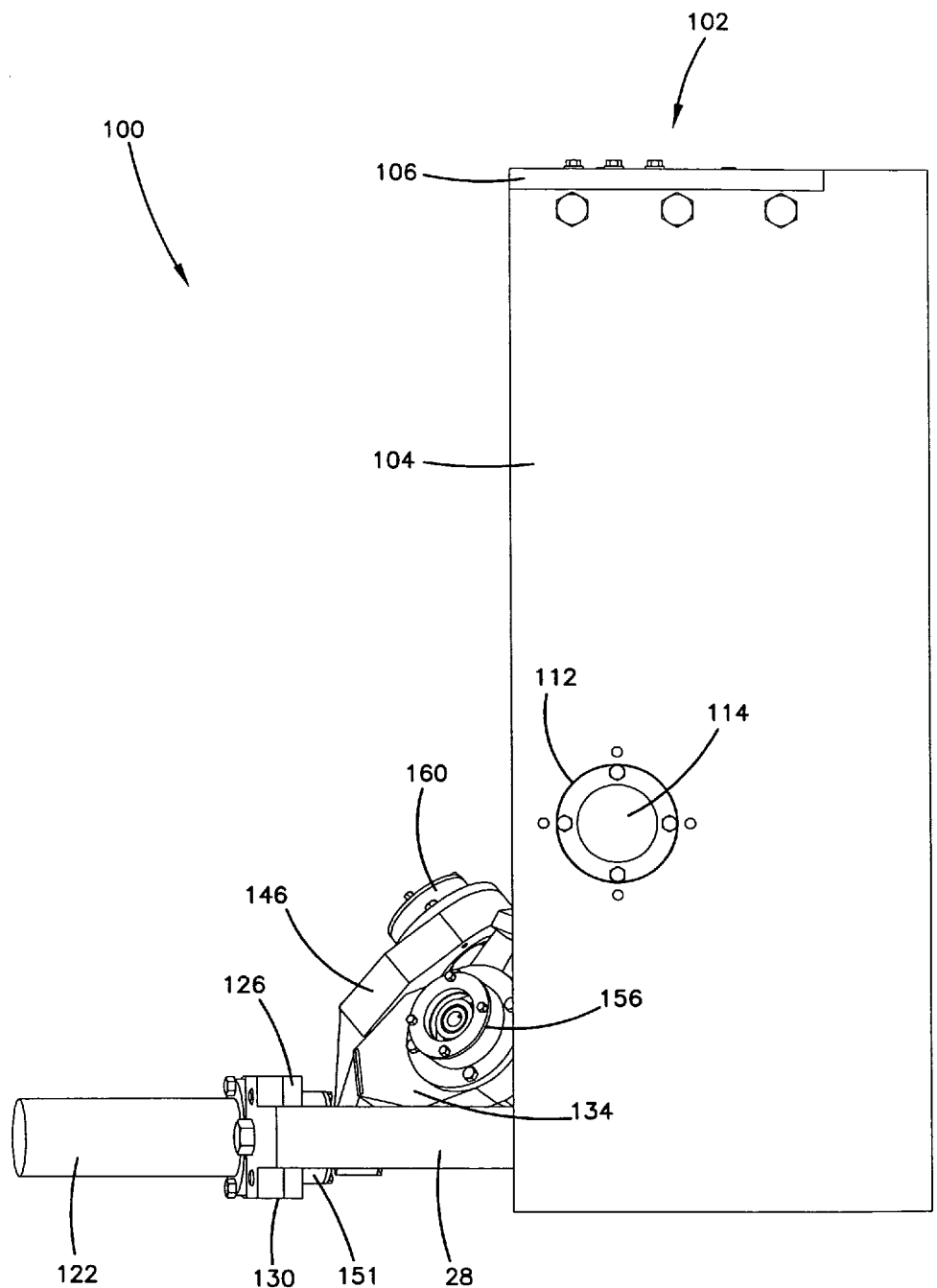
FIG. 2 shows a right side elevational view of the scanner shown in FIG. 1.
Figure 3:
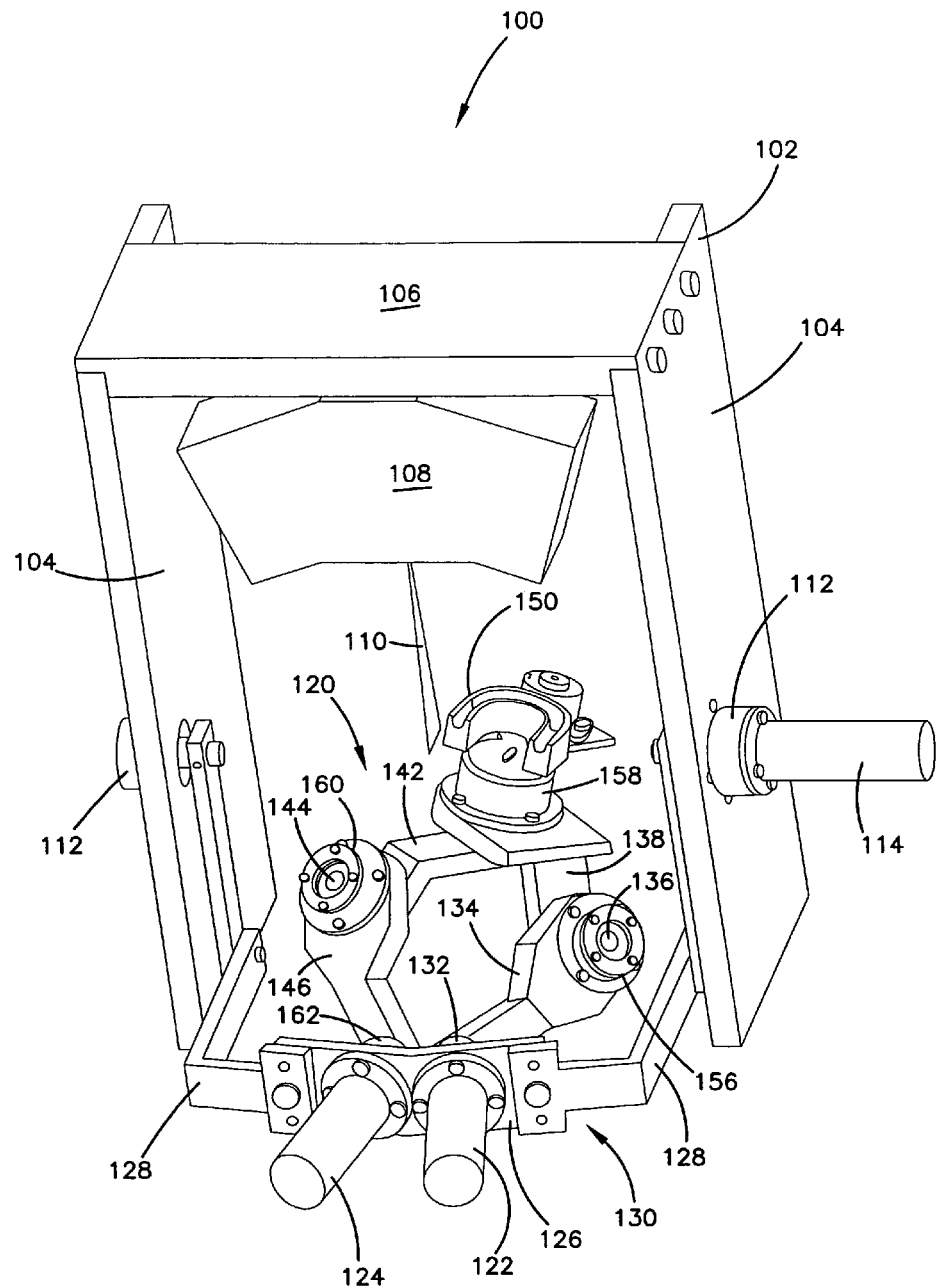
FIG. 3 shows a front top perspective view of the scanner shown in FIG. 1.
Figure 4:
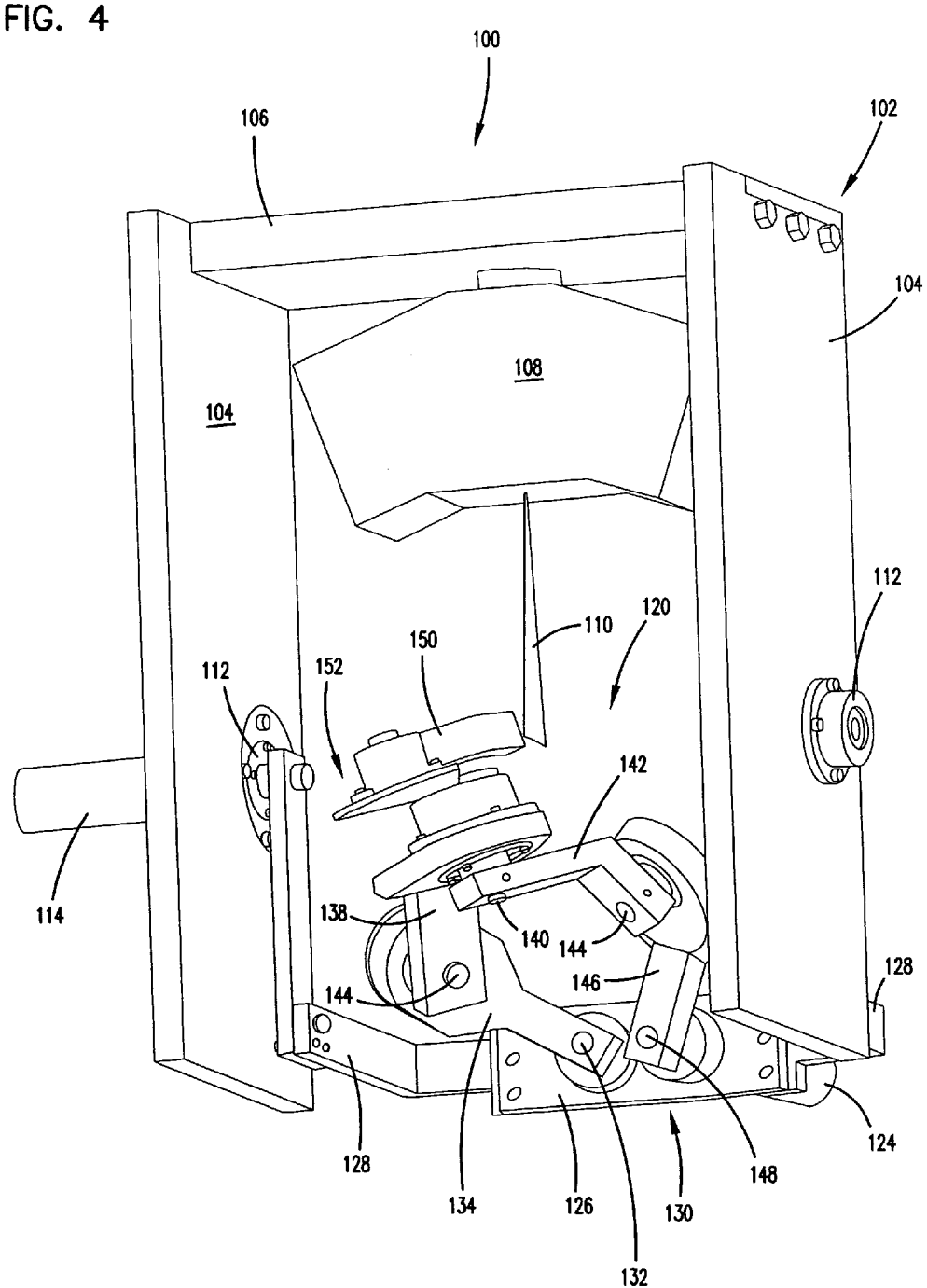
FIG. 4 shows a rear bottom perspective view of the scanner shown in FIG. 1.
Figure 5:
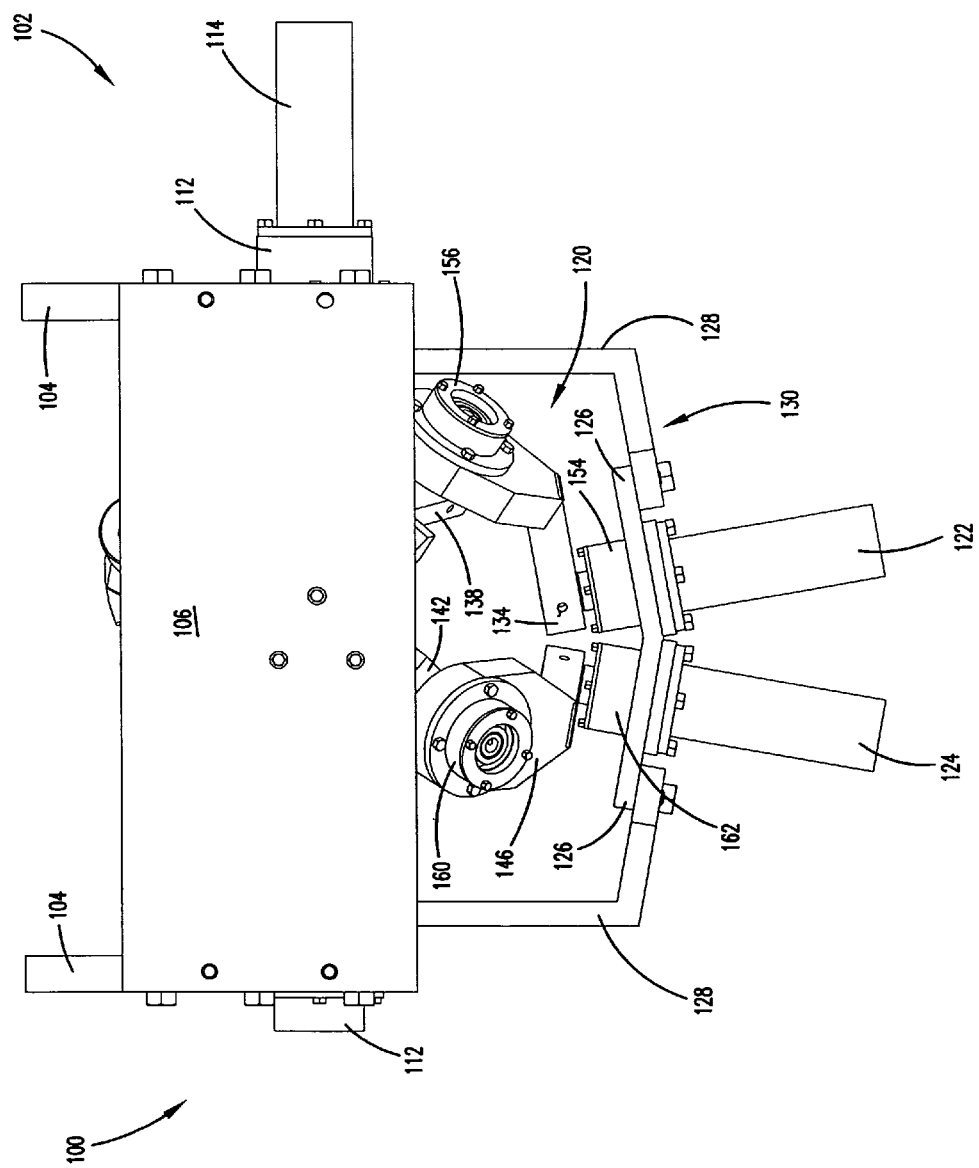
FIG. 5 shows a top plan view of the scanner shown in FIG. 1.
Figure 6:
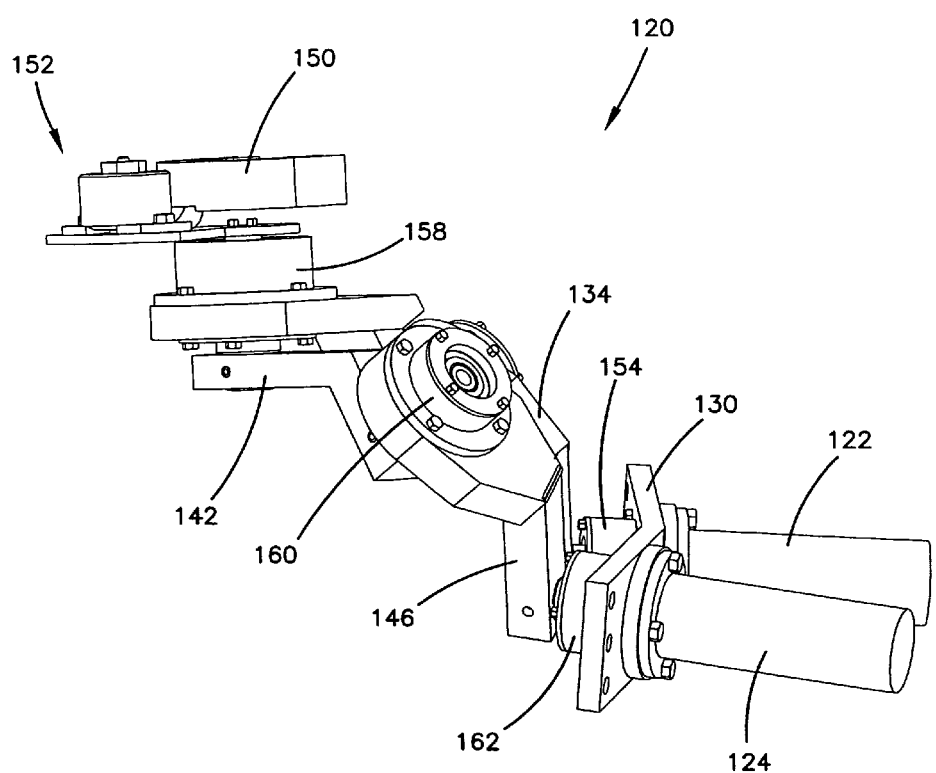
FIG. 6 shows a left side perspective view of the linkage for the scanner shown in FIG. 1.
Figure 7:
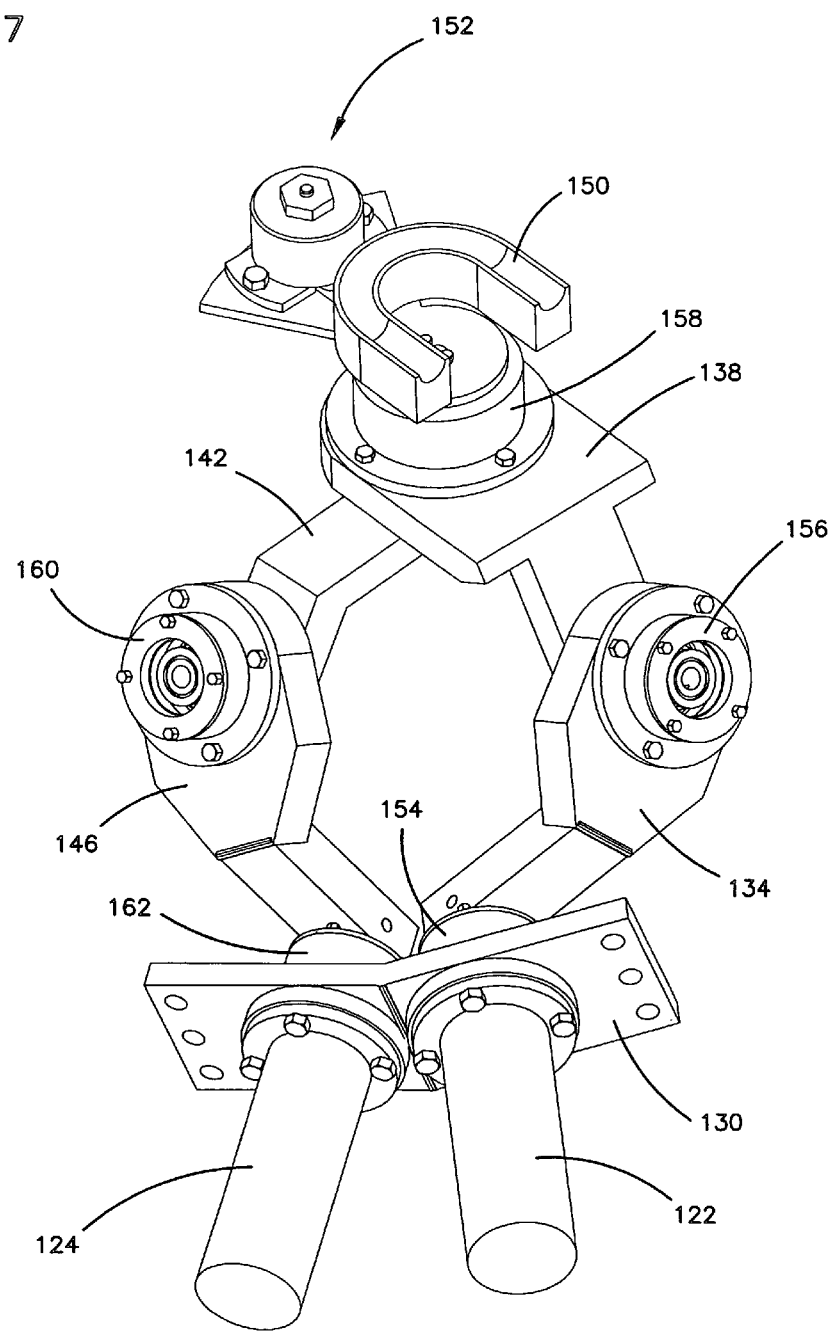
FIG. 7 shows a top perspective view of the linkage shown in FIG. 6.
Figure 8:
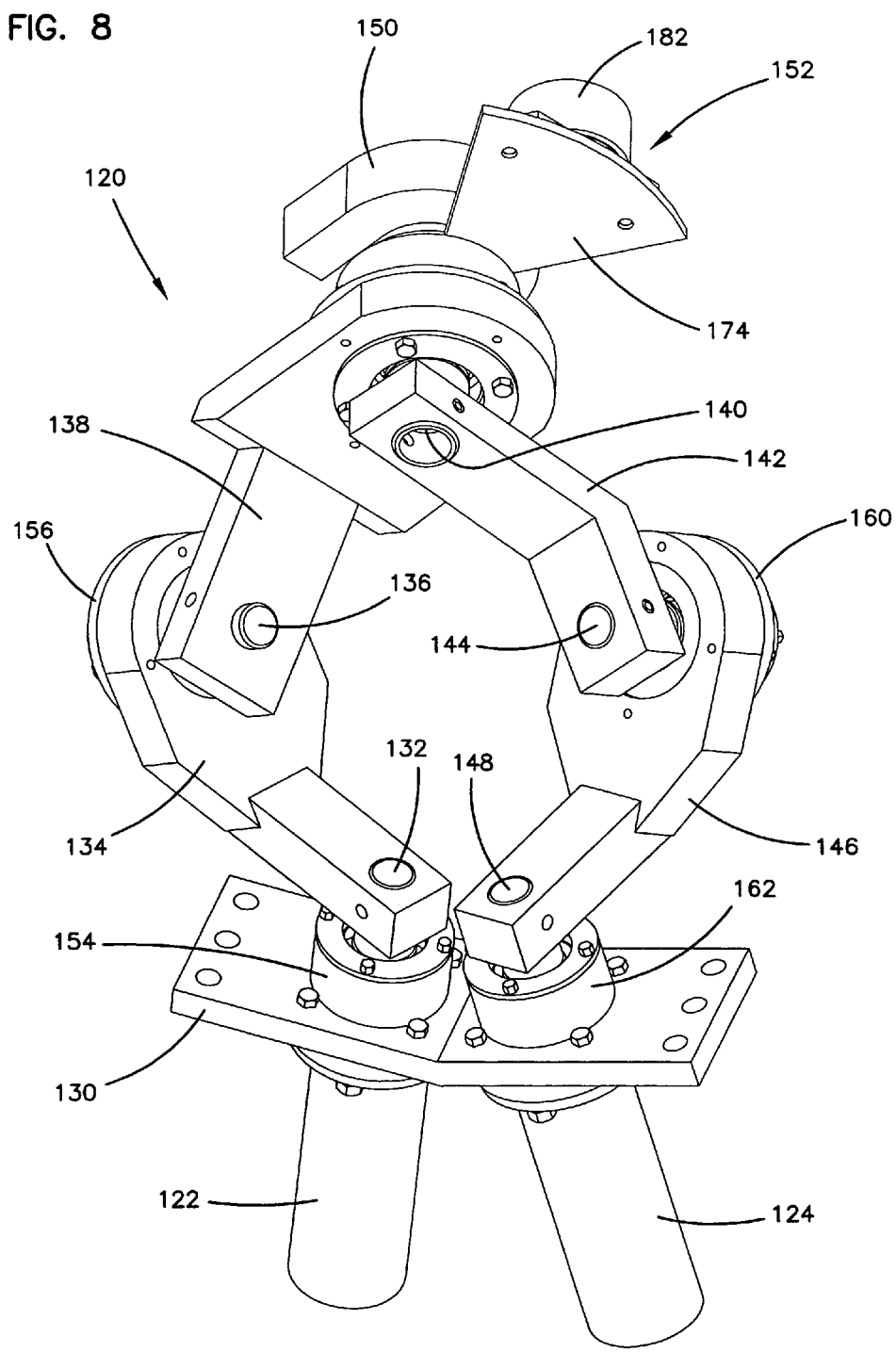
FIG. 8 shows a bottom perspective view of the linkage shown in FIG. 6.
Figure 9:
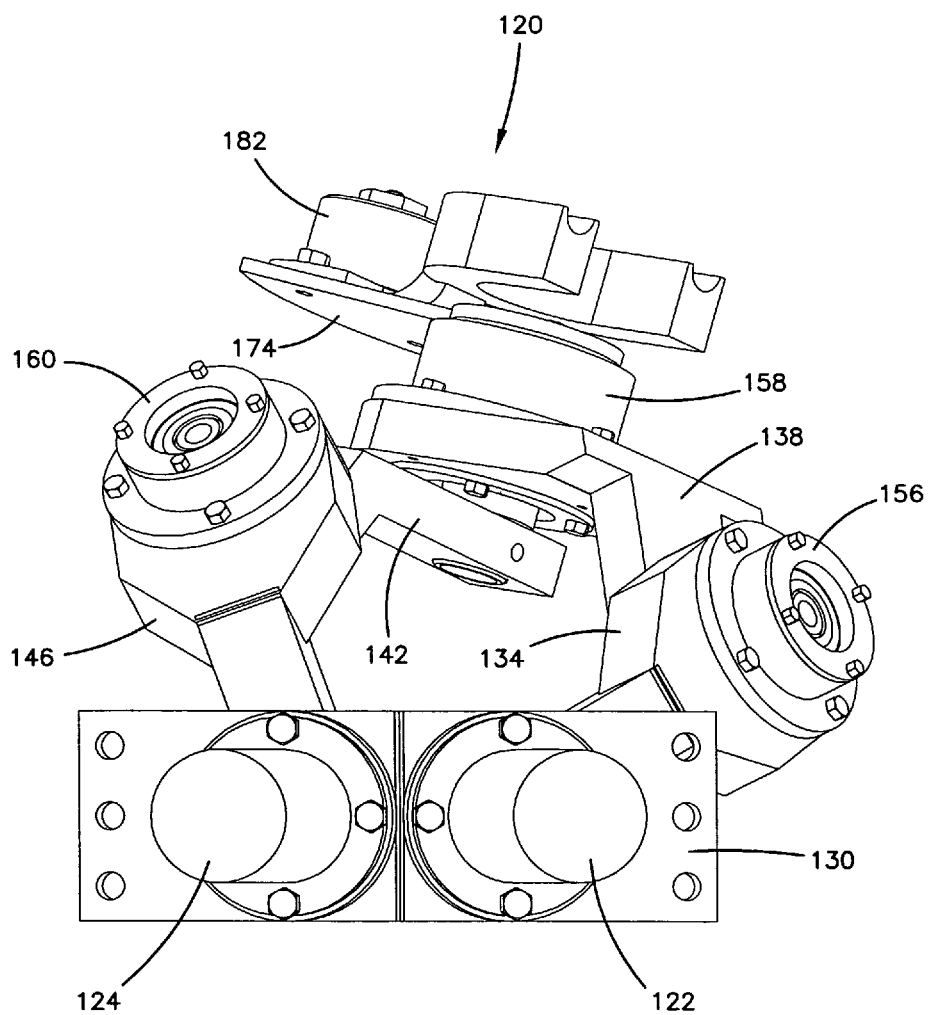
FIG. 9 shows a front elevational view of the linkage shown in FIG. 6.
Figure 10:
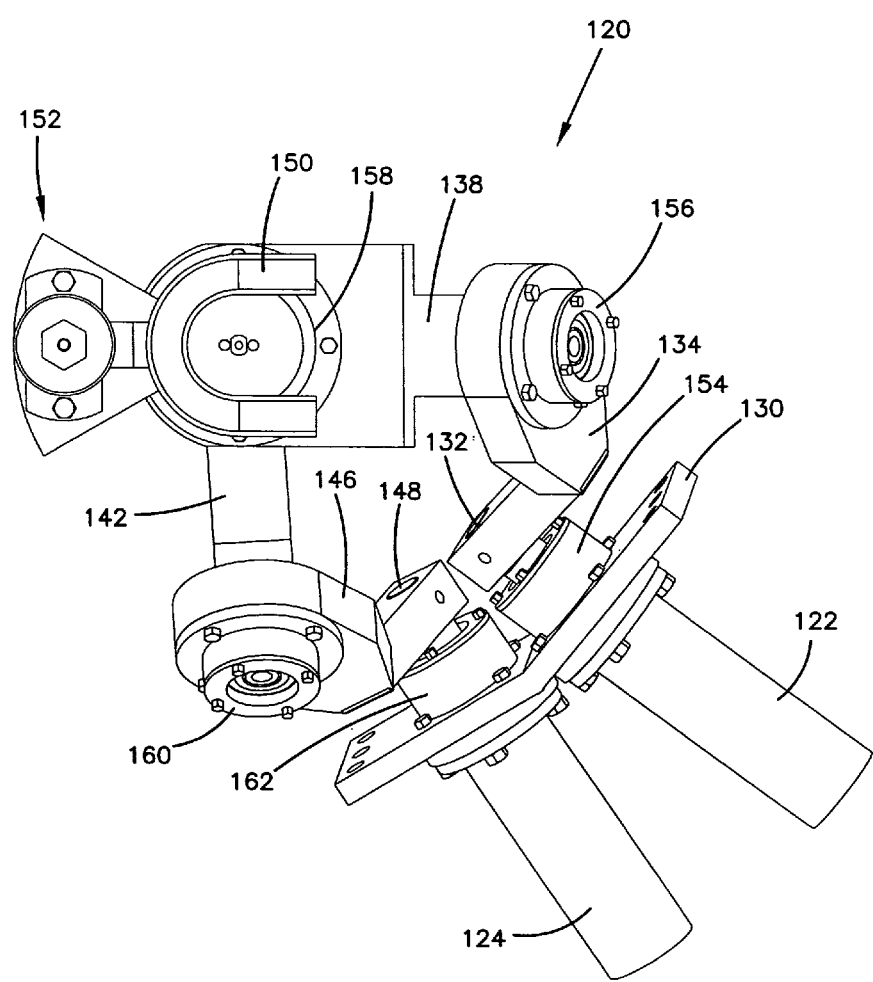
FIG. 10 shows a top plan view of the linkage shown in FIG. 6.

Referring now to the drawings, and in particular FIG. 1, there is shown a scanning apparatus, generally designated 100. The scanning apparatus 100 is particularly suited for positioning and scanning dental models for digitizing the dental molds. As shown in FIGS. 1–5, the scanning apparatus 100 includes a support frame 102 having spaced apart uprights 104 supporting an upper cross support 106. A laser scanner device 108 is mounted to the underside of the cross support 106 and emits a scanner beam 110, shown more clearly in FIGS. 3 and 4, at the object to be scanned. A spherical linkage 120 is utilized to move a dental model 150 in scanning sweeps beneath the laser scanner 108 so that its surface may be scanned completely. The linkage 120 is mounted to the frame 102 on a pivoting arm 128 extending from each upright 104. The pivoting arm 128 is mounted on bearing assemblies 112 and is driven by a motor 114 from at least one side of the arm 128. The rotational axis of the arm 128 preferably passes substantially through the bearing assemblies 112, motor 114 and the supported article. In a preferred embodiment, the motor 114 is a direct current servo motor with an encoder, such as Model 3863, available from MicroMO. However other types of motors, such as a stepper motor, giving a precise stopping position may also be utilized. The bearing assemblies 112 utilize two tapered roller bearings housed in a bearing box in a preferred embodiment.

The linkage 120 is mounted directly to the arm 128 and utilizes a plate 126 mounted to the arm 128 so that the arm and plate 126 form the ground link 130 of the linkage 120. As shown most clearly in FIGS. 6–10, the linkage 120 is a five bar spherical closed loop serial linkage that provides improved support and positioning. The linkage 120 provides for scanning the entire surface of a dental model held in the dental model tray 150 and without interrupting the scanning beam 110. The spherical linkage 120 provides for paths of motion that are more compatible for scanning the typical dental model as the teeth are arranged in an arcing configuration more naturally suitable to curved scanning than to the straight line sweeps of a linear scanning pattern. A dental model tray 150 is aligned proximate one of the rotational axes between two of the linkage links and allows for moving the dental model through the scanner beam 110 to provide complete scanning coverage of the model. In addition, as the linkage 120 forms a closed loop, the scanning is more accurate as there are no nonsupported serial links extending outward that might have a greater degree of error due to tolerances, flexure, and compounding of these problems along a multi-link serial linkage.

Figure 12:
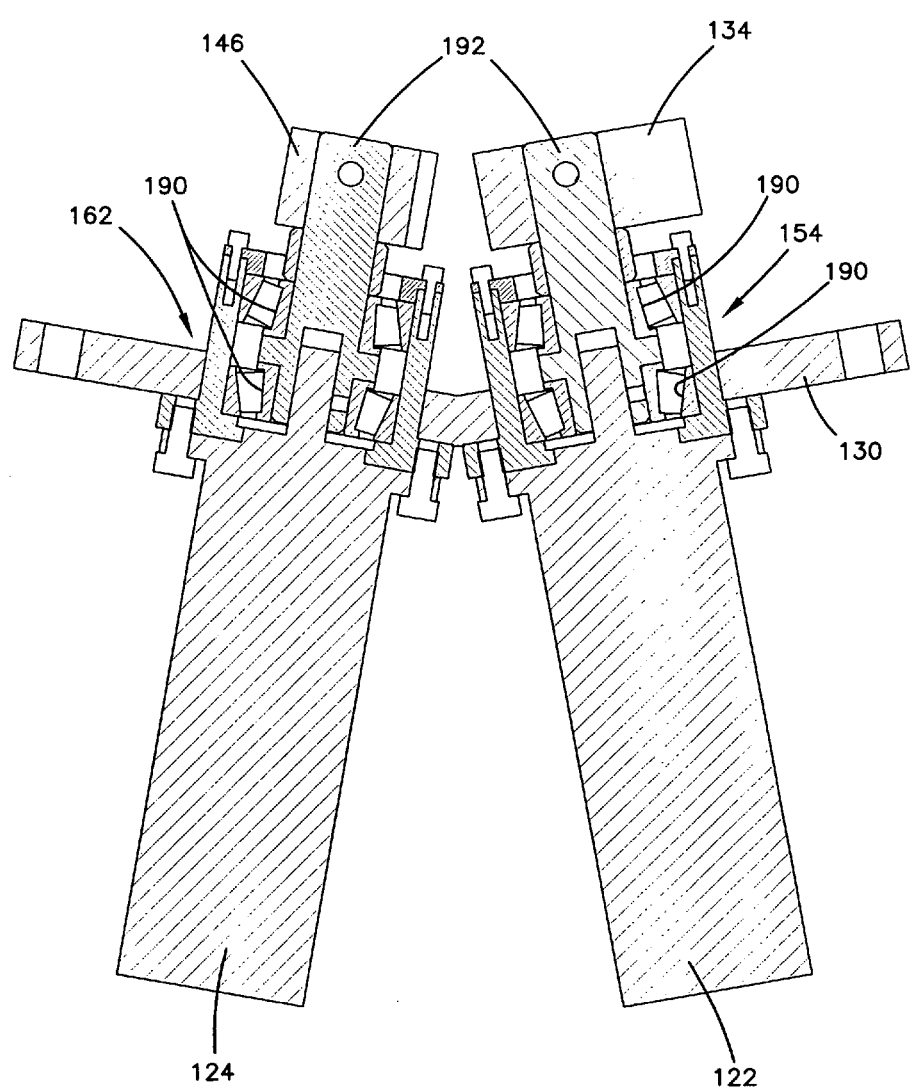
FIG. 12 shows a top sectional view of the linkage drive motors for the scanner apparatus shown in FIG. 1.

As the linkage 120 includes two degree of freedom, two motors 122 and 124 are provided as drivers to input motion to the linkage 120. As shown in FIG. 12, the motors 122 and 124 are brushless dc servo motors with encoders in a preferred embodiment, such as MicroMO Model 3564. In the embodiment shown, both motors drive the links pivotally mounted to the ground link 130. The first motor 122 is aligned with a first joint 132 connecting the ground link 120 to second link 134. The first joint 132 has a rotational axis extending through the spherical center of the linkage 120, as do all the other rotational axes of the various joints. A bearing assembly 154 provides ease of rotation between the first and second links 130 and 134. Referring now to FIGS. 6–10, the ground link 130 connects to the second link 134 at the first joint 132. The second end of the second link 134 pivotally connects to a first end of a third link 138 at a second joint 136. The second joint 136 also has a rotational axis that passes through the spherical center of the spherical linkage 120. A bearing and encoder assembly 156 provides for accurate rotation between the second link 134 and the third link 138. A second end of the third link 138 connects to a first end of a fourth link 142 at joint 140. The joint 140 has a rotational axis extending through the spherical center of the spherical linkage 120. The joint 140 also includes a bearing assembly 158 with the dental model tray 150 and dental model tray clamping mechanism 152 mounted thereon. The second end of the fourth link 142 connects to the first end of the fifth link 146 at a joint 144. The joint 144 has a rotational axis extending through the center of the serial linkage 120 and intersecting the other rotational axes. A bearing and encoder assembly 160 provides for ease of rotation between the fourth link 142 and the fifth link 146. A second end of the fifth link 146 connects to the first ground link 130 at a fifth joint 148. The fifth joint 148 is aligned with the shaft of the motor 124 and through the center of the spherical linkage 120.

Figure 11:
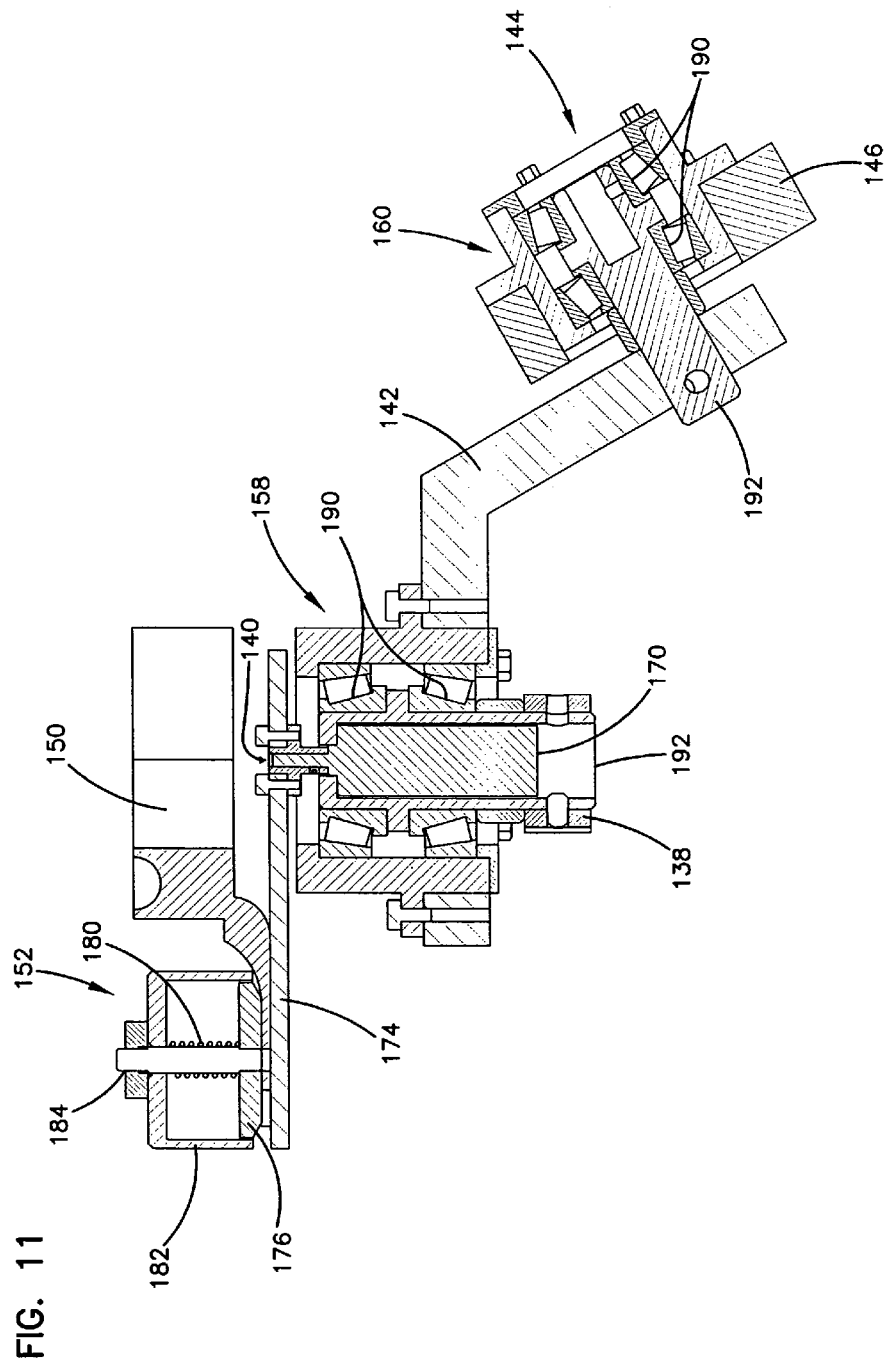
FIG. 11 shows a sectional view taken through the dental tray clamp and two adjacent links for the scanner apparatus shown in FIG. 1.

Referring to FIG. 11, the clamping mechanism 152 mounts to the top of the bearing assembly 140. The bearing assembly 140 includes two sets of tapered-type bearings 190 and supporting a bearing shaft 192. A motor 170 having an encoder, such as MicroMO Model 1628, rotates the clamping mechanism 152 so that the dental models supported in the tray 150 may be rotated as the linkage 120 moves through its ranges of motion. This configuration provides an additional degree of freedom and improved access and coverage of objects to be scanned. The dental tray 150 mounts on a clamping plate 154 and is held in position by a press plate 176 to provide a quick disconnect. A clamping housing 182 pushes down onto a clamping spring 180 to eliminate looseness and maintain the dental tray 150 tightly against the press plate 176 aligned beneath the scanning beam. A clamping mount 184, such as a bolt and nut, receives the compression spring 180, the housing 182, the press plate 176 and the dental tray 150. The clamping mechanism 152 is offset from the axis of the third joint 140. However, this arrangement moves the dental tray 150 so that it is substantially above and aligned with the axis passing through the third joint 140. The scanned object is supported outside the sphere of the spherical linkage 120, thereby allowing the linkage 120 to be more compact than if the object were supported at the interior of the sphere. This configuration places the object to be scanned substantially at the rotational axis of the arm 128, so that the object remains in the depth of field of the scanner 108, as shown in FIG. 1.

As can also be seen in FIG. 11, the other bearing assemblies, such as bearing assembly 160 mounted at the joint 144 between the fourth link 142 and the fifth link 146 also includes a housing including two sets of tapered bearings 190 supporting a bearing shaft 192. Although the bearing assemblies provide some additional weight, the nature of the spherical linkage provides additional support at both ends of each link so that the precision is not adversely affected and accurate scanning is achieved.

Referring to FIG. 12, the input drive motors 122 and 124 for the linkage 120 include associated bearing assemblies 154 and 162 respectively. Each of the bearing assemblies 154 and 162 includes two sets of tapered bearings 190 supporting the bearing shaft 192. The motors 122' and 124 are aligned with the rotational axis for each of the bearing assemblies 154 and 162 and intersect at the spherical center of the linkage 120. Both drive motors 122 and 124 are mounted to the ground link 130 in the embodiment shown. However, it can be appreciated that in other configurations, it may be necessary to change mounting locations for one or both of the motors 122 and 124 to other joints of the linkage 120.

The scanner apparatus 100 provides for four degrees of freedom to meet the scanning requirements for efficiently scanning a dental model. All of the motors and encoders is connected to a central processor or controller to coordinate the various inputs and position the linkage 120 as desired. The angle of the ground link 130 may be changed by driving the motor 114, to provide a first degree of freedom. The motor 114 and arm 128 control the pitch angle relative to the scanner 108. In addition, the position of five bar linkage 120 may be altered by driving one or both of the motors 122 and 124, providing two more degrees of freedom. The motors 122 and 124 provide two translational degrees of freedom. Finally, the position of the clamping mechanism 152, and therefore the dental model 150, may also be rotated relative to the linkage 120 by the motor 140, providing a fourth degree of freedom. The motor 140 controls the yaw angle relative to the scanner 108. The four degrees of freedom provides controlled scanning access to the surface of objects that are being scanned while matching the needs of a typical laser scanner. Such a scanning apparatus 100 having four degrees of freedom is also cheaper than more complicated five or six degree of freedom mechanisms. Moreover, as the object is placed outside the sphere of the spherical closed loop linkage 120, the links do not pass through the scanning beam 110 and complete coverage can be accomplished.

As the linkage 120 is a closed loop type linkage, there is not an unacceptable degree of flexure or inaccuracy due to tolerances that occur and compound with multi-link linkages that do not have a closed loop. The spherical linkage provides more compatible paths of motion for scanning curved objects and minimizes the workspace required for the scanning system 100. Although the size required will depend on the scanner 108 which is used and its focus range, for the embodiment shown using a laser scanner 108 Model RPS 150, manufactured by Geometric Research Incorporated, a spherical linkage 120 having a radius of about four inches, giving a scanning radius of about six inches has been achieved. A frame width of approximately 15" and a height of approximately 20" is also achieved. Such economies of space provide for more viable use for the scanning apparatus, such as a tabletop or desktop version which could be used in a dental office.

Each link may be defined by the included angle between its joints, which remains constant as the linkage 120 is moved and as the radius of a link is varied. In the embodiment shown, the first link 130 is a 20 degree link, the second link 134 and the fourth link 146 are 50 degree links, and the third link 138 and fourth link 142 are 60 degree links. Therefore, the linkage 120 is symmetrical about the first link 130. Such a configuration simplifies manufacturing, scanning calculations and plot planning over non-symmetrical linkages.

Although the scanner apparatus 100 is shown for use in digitizing dental models, it may be used for many other biomedical and non-biomedical applications requiring movement through a small depth of field with four degrees of freedom. Other typical applications include, but are not limited to, scanning vertebral bodies in the spine, scanning cast or machined elements, coordinate measuring systems, or path generation for tools and instruments.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A scanning apparatus, comprising:
   a scanner having a measuring device for measuring the shape of a scanned article;
   a linkage comprising:
      a first ground link;
      a second link rotatably mounted to the first link about a first axis;
      a third link rotatably mounted to the second link about a second axis;
      a fourth link rotatably mounted to the third link about a third axis;
      a fifth link rotatably mounted to the fourth link about a fourth axis and rotatably mounted to the first link about a fifth axis;
      an article holder mounted to one of the links adapted for supporting an article to be scanned exterior of a sphere defined by the linkage;
   wherein the seamier and article holder are movable relative to one another to scan the surface of the article.

2. A scanning apparatus according to claim 1, wherein the links are adapted for moving along pats of motion that avoid the scanner beam.

3. A scanning apparatus according to claim 1, wherein the article holder is adjustable to accommodate a range of article shapes and sizes.

4. A scanning apparatus according to claim 1, wherein the article holder is rotatably mounted to the linkage.

5. A scanning apparatus according to claim 4, wherein the article holder further comprises a drive motor for rotating the article holder relative to the linkage.

6. A scanning apparatus according to claim 1, wherein the article holder is adapted for holding the article in alignment with an axis of rotation between two of the links.

7. A scanning apparatus according to claim 1, wherein the first ground link is rotatably mounted to a scanner support.

8. A scanning apparatus according to claim 1, wherein the linkage is adjustably mounted relative to the scanner to provide a third degree of freedom.

9. A scanning apparatus according to claim 1, wherein the article holder is adjustably mounted relative to the linkage to provide a third degree of freedom.

10. A scanning apparatus according to claim 8, wherein the article holder is adjustably mounted relative to the linkage to provide a fourth degree of freedom.

11. A scanning apparatus according to claim 1, wherein the linkage includes a first driver and a second driver.

12. A scanning apparatus according to claim 11, wherein the linkage mounts to an arm adjustably mounted to a scanner support and wherein the arm includes a third driver.

13. A scanning apparatus according to claim 11, wherein the article holder is adjustably mounted relative to the linkage and wherein the article holder includes a third driver.

14. A scanning apparatus according to claim 13, wherein the article holder is adjustably mounted relative to the linkage and wherein the article holder includes a fourth driver.

15. A scanning apparatus according to claim 7, wherein the linkage includes a first pair of symmetrical links having a first included angle.

16. A scanning apparatus according to claim 15, wherein the linkage includes a second pair of symmetrical links having a second included angle.

17. A scanning apparatus according to claim 7, wherein the linkage includes a first driver mounted to a first axis of one of the links and a second driver mounted to a second axis of the one of the links.

18. A scanning apparatus according to claim 7, wherein the joints include encoders in communication with a controller for coordinating actuation and movement.

19. A scanning apparatus according to claim 7, wherein the support assembly includes a five bar spherical closed loop linkage.

20. A scanning apparatus according to claim 19, wherein the linkage is rotatably mounted relative to the scanner.

21. A scanning apparatus according to claim 19, wherein the support assembly further comprises an article holder rotatably mounted to the linkage.

* * * * *